United States Patent [19]

Duerholz et al.

[11] Patent Number: 5,087,454

[45] Date of Patent: Feb. 11, 1992

[54] IBUPROFEN TABLET

[75] Inventors: Joanne R. Duerholz, Medford; Dolores DiMaria, Vineland; Robert G. Blank, Hammonton, all of N.J.

[73] Assignee: American Home Products Corporation, New York, N.Y.

[21] Appl. No.: 559,862

[22] Filed: Jul. 30, 1990

[51] Int. Cl.$^5$ ............................ A61K 9/14; A61K 9/20
[52] U.S. Cl. .................................... 424/464; 424/465; 424/470; 424/474; 424/479; 424/489; 424/499; 514/960
[58] Field of Search .................... 424/464, 465, 470

[56] References Cited

U.S. PATENT DOCUMENTS

| | | | |
|---|---|---|---|
| 4,781,925 | 11/1988 | Michelucci et al. | 424/465 |
| 4,837,031 | 6/1989 | Denton | 424/464 |
| 4,904,477 | 2/1990 | Ho et al. | 424/465 |
| 4,911,921 | 3/1990 | Denton et al. | 424/470 |

Primary Examiner—Thurman K. Page
Assistant Examiner—James M. Spear
Attorney, Agent, or Firm—John W. Routh

[57] ABSTRACT

Ibuprofen tablets/caplets formed by wet granulation of the ibuprofen characterized by a dissolution profile maintained stable on aging by incorporating croscarmellose sodium separately into the wet granulation and the compression mix and further incorporating sodium lauryl sulfate into the compression mix.

1 Claim, No Drawings

IBUPROFEN TABLET

BACKGROUND OF THE INVENTION

This invention relates to improved ibuprofen tablets/caplets characterized by a dissolution profile maintained stable on aging for up to two years. The tablets/caplets of the invention are formed by wet granulation of the ibuprofen to provide the dried base granulation for the compression mix.

In the past, most ibuprofen compressed tablets have been prepared from a wet granulation of a binder, such as starch, and ibuprofen which is dried, mixed with lubricants and disintegrating agents and compressed into tablets. Ibuprofen, however, is known to have unique dissolution characteristics when incorporated into compressed tablets. One attempt to provide a more stable dissolution profile to ibuprofen compressed tablets is described in U.S. Pat. No. 4,904,477 issued Feb. 27, 1990. That patent discloses a spray dried ibuprofen composition comprising finely divided ibuprofen in a gelatinized starch martrix of a generally spherical shape. The spray dried compositions comprise ibuprofen, as a disintegrant crospovidone, croscarmellose sodium and/or sodium starch glycolate, pregelatinized starch, colloidal silica and as a wetting agent polyvinylpyrrolidone and/or sodium lauryl sulfate. The patent further discloses that the spray dried ibuprofen can be incorporated into a compression mix together with starch, a disintegrant, such as croscarmellose sodium, and a wetting agent, such as sodium lauryl sulfate, to make compressed tablets. Because of the pertinence of U.S. Pat. No. 4,904,477, the disclosure of the patent is incorporated by reference herein in its entirely.

SUMMARY OF THE INVENTION

The present invention overcomes the deficiencies in dissolution characteristics of ibuprofen containing compressed tablets and provides a dissolution profile maintained stable on aging. The present invention thus represents an improvement in an ibuprofen compressed tablet/caplet containing about 50% to about 70% by weight based on the weight of the tablet/caplet core of ibuprofen formed by (a) wet granulating the ibuprofen with standard excipients including starch to provide a dry base granulation, (b) formulating a compression mix containing the dry base granulation and standard lubricants and excipients, and (c) tabletting the compression mix. The improvement of the invention comprises (1) separately incorporating into each of the wet granulation and the compression mix about 1% to about 2% by weight based on the weight of the compressed tablet/caplet core of croscarmellose sodium and (2) incorporating into the compression mix about 0.05% to about 0.15% by weight based on the weight of the compressed tablet/caplet core of sodium lauryl sulfate. By tablet/caplet core is meant the tablet/caplet prior to sealing, coating and polishing.

DETAILED DESCRIPTION OF THE INVENTION

The ibuprofen is available commercially, for example, from Ethyl Corporation, Baton Rouge, La. A suitable pharmaceutical grade is marketed with a particle size of approximately 38 microns passing through a 4 mesh screen.

Croscarmellose sodium is a cross-linked polymer of carboxymethylcellulose sodium and is available in Type A and Type B depending upon the degree of substitution. Type A is preferred for the compositions of this invention. It is sold under the trade name ACDISOL and is available from FMC Corporation, 200 Market Street, Philadelphia, Pa. 19103, U.S.A.

Pregelatinized starch is starch that has been chemically and/or mechanically processed to rupture all or part of the granules separated from the mature grain of corn in the presence of water. It is available from National Starch and Chemical Corp., Bridgewater, N.J. U.S.A. as STARCH 1551.

The colloidal silica is a commercial product and is available commercially in USP and NF grades. It is marketed by Degussa Corp., Teterboro, N.J. U.S.A. and a suitable grade is marketed under the tradename AEROSIL 200.

Sodium lauryl sulfate is a commercial product in USP grade. Preferably it is used in powder form to promote blending and is available from Albright Wilsen, 180 Old Tappan Road, Old Tappan, N.J., U.S.A., under the tradename EMPICOL, and a suitable grade is EMPICOL 0303.

This invention will be further illustrated by the following examples in which the compression mix for sugar coated tablets was prepared using the procedures described therein.

EXAMPLE 1

Base Granulation

In this example the following ingredients were used to form the base granulation.

| Ingredient | Milligrams per Tablet | Grams per 50,000 Tablets |
|---|---|---|
| Ibuprofen USP (4 mesh) | 200.0 | 10,000 |
| Starch NF | 78.9 | 3945 |
| Colloidal Silica | 1.0 | 50 |
| Pregelatinized Starch NF | 18.8 | 940 |
| Croscarmellose Sodium, Type A NF | 5.0 | 250 |
| Total | 303.7 | 15,185 |
| Purified Water, deionized | | 4,926 ml. |

The dry ingredients were weighed out and placed in a DIOSNA granulator and the granulator was started to premix the dry ingredients for 2 minutes and thirty seconds. Water was then added slowly over a period of 2 minutes and five seconds and the granulator was run for an additional four minutes and fifteen seconds.

The wet granulation was separated into two approximately equal portions and the two portions were separately charged to a fluid bed dryer. The first portion was dried for about 19 minutes using an inlet air temperature of 140° F. at which time the moisture content of the granulate was 2.4%. The second portion was dried for 25 minutes using an air inlet temperature of 140° F. The moisture content of the second portion was 2.2%.

The screen analyses of the two portions of the base granulation from the fluid bed dryer are given separately and when admixed as follows. The screen analyses were carried out after using a 16 mesh Stokes Oscillator screen.

| Mesh | % Retained on | | | | | |
| | 14 | 20 | 40 | 60 | 80 | Pan |
|---|---|---|---|---|---|---|
| Portion 1 | — | 1 | 13 | 31 | 28 | 27 |

-continued

| Mesh | % Retained on | | | | | |
|---|---|---|---|---|---|---|
| | 14 | 20 | 40 | 60 | 80 | Pan |
| Portion 2 | — | 1 | 6 | 23 | 25 | 45 |
| Combined | — | 1 | 9 | 30 | 27 | 33 |

Compression Mix

The following ingredients were used to form a first batch of the compression mix. The base granulation was the combined portions.

| Ingredient | Milligrams per Tablet | Grams per 12,000 Tablets |
|---|---|---|
| Base Granulation | 303.7 | 3644.4 |
| Croscarmellose Sodium, Type A NF | 5.0 | 60.0 |
| Pseudoephedrine HCl | 30.0 | 360.0 |
| Stearic Acid USP | 1.8 | 21.6 |
| Colloidal Silica | 0.6 | 7.2 |
| Corn Starch | 7.0 | 84.0 |
| Sodium Lauryl Sulfate | 0.5 | 6.0 |
| Total | 348.6 | 4183.2 |

The procedure for forming the compression mix was first to screen enough of the base granulation through 30 mesh to obtain about 109 grams of fines, mix the fines with the stearic acid powder, colloidal silica, starch and sodium lauryl sulfate, bag mix and then screen the mix through 30 mesh. The remaining base granulation, the pseudoephedrine and the croscarmellose sodium were added to the fines mix and blended in a twin shell V blender for five minutes.

Two additional batches were made similarly as above and the three batches were bag mixed together and compressed on a Versa Press. The compression mix prior to compression into tablets had a moisture content of 2%, an angle of repose of 26° and a bulk density of 0.48 grams per cubic centimeters.

The tablets from the press were oval in shape, weighed (average) 349 milligrams, were 0.187–0.192 inches thick and were of 8–10 hardness (Strong Cobb Units) with good friability (USP Test).

The tablets were then sealed, sugar coated, and polished using a conventional procedure and conventional ingredients. The coated tablets were tested for dissolution characteristics in accordance with the USP test method and the time in minutes at which all 6 tablets were 55% dissolved was no greater than 9 minutes. The dissolution test was repeated one year later after separate storage of the tablets for one year at room temperature and at 37° C. The time in minutes at which all 6 tablets stored at room temperature for a year were 55% dissolved again was no greater than 9 minutes, indicating an excellent dissolution profile, and the time in minutes at which all 6 tablets stored at 37° C. for one year were 55% dissolved was no greater than 16 minutes.

EXAMPLE 2

In this example, sugar coated tablets were produced which contained ibuprofen as the only medicament, the pseudoephedrine hydrochloride being omitted from the compression mix.

The base granulation has the same formula as described above in Example 1 although the batch was larger, i.e. enough to make 645,000 tablets. A larger granulator and fluid bed dryer were used and the dried granulation was sized through a Colton Granulator fitted with a #16 mesh stainless steel screen and the dried granulation had a moisture content of 2.1%.

Compression Mix

The following ingredients were used to form the compression mix.

| Ingredient | Milligrams per Tablet |
|---|---|
| Base Granulation | 303.7 |
| Croscarmellose Sodium, Type A NF | 5.0 |
| Stearic Acid USP | 1.8 |
| Colloidal Silica | 0.6 |
| Corn Starch | 7.0 |
| Sodium Lauryl Sulfate | 0.5 |
| | 318.6 |

The procedure for forming the compression mix was first to blend 3% by weight of the base granulation, the stearic acid powder and colloidal silica in a planetary type mixer for 10 minutes at slow speed. This preblend was passed through a comminuter and then all the ingredients including the preblend were passed through a #12 mesh stainless steel screen into a PK Blender and mixed for 20 minutes without the intensifier bar.

The compression mix was compressed into round tablets on a 75 station tablet press on freshly polished punches at 4,000 tablets per minute. The compression physicals for the tablets were for average tablet weight, 319 mg; thickness, 0.209–0.211 inch; hardness, 5–7 Strong Cobb Units; and friability 0.56% at 30 minutes.

The tablets were then sealed, sugar coated, and polished using a conventional procedure fully described in Example 12 of U.S. Pat. No. 4,904,477. A comparison was made of the dissolution characteristics of the tablets of Example 2 of this application and of samples of Example 12 of U.S. Pat. No. 4,904,477. The compositions of the respective tablets from Examples 2 and 12 are given below.

| U.S. Pat. No. 4,904,477 Example 12 % Ingredients In Spray Dried Powder | | Example 2 % Ingredients In Base Granulation |
|---|---|---|
| TABLET COMPOSITION Ibuprofen Component | | |
| 10.25 | Pregelatinized Starch | 6.19 |
| 3.5 | Croscarmellose Sodium | 1.65 |
| 0.25 | Colloidal Silica | 0.33 |
| 1.00 | Povidone | — |
| 85.00 | Ibuprofen | 65.85 |
| — | Starch NF | 25.98 |
| Milligrams Per Tablet | | Milligrams Per Tablet |
| | Compression Mix Ingredients | |
| 236.0 | Spray Dried Powder Base Granulation | 303.7 |
| 22.4 | Pregelatinized Starch | |
| 22.4 | Starch | 7.0 |
| 18.0 | Croscarmellose Sodium | 5.0 |
| 0.65 | Colloidal Silica | 0.6 |
| 0.75 | Sodium Lauryl Sulfate | 0.5 |
| 1.80 | Stearic Acid | 1.8 |
| 302.00 | | 318.6 |

The sugar coating, sealing and polishing operations were the same for both tablet batches.

The coated tablets of Example 12 of U.S. Pat. No. 4,904,477 and of Example 2 of this application were subjected to both the USP method for determining dissolution times and to the FDA suggested method. The USP method prior to 1988 required 55% dissolution in 30 minutes using a basket rotating at a speed of 150 RPM. The requirement was raised in 1988 to 75% dissolution in 30 minutes using a basket rotating at a speed of 150 RPM. The FDA suggested method on the other hand requires 80% dissolution in 60 minutes although under less severe conditions, i.e. a paddle speed of only 50 RPM.

The dissolution results are shown in the following table. The data in the table indicate that over a two-year period the dissolution times of the coated tablets of Example 2 were relatively constant in both the USP method and the suggested FDA method for determining dissolution times.

We claim:

1. In an ibuprofen compressed tablet/caplet containing about 50% to about 70% by weight based on the weight of the tablet/caplet core of ibuprofen formed by (a) wet granulating the ibuprofen with an excipient comprising starch to provide a dry base granulation (b) formulating a compression mix containing the dry base granulation and an excipient comprising starch, and (c) tabletting the compression mix, the improvement which comprises providing a compressed tablet having an improved dissolution profile maintained stable on aging by (1) separately incorporating into each of the wet granulation and the compression mix about 1% to about 2% by weight based on the weight of the compressed tablet core of croscarmellose sodium and (2) incorporating into the compression mix about 0.05 to about 0.15% by weight of the compressed tablet core of sodium lauryl sulfate.

* * * * *

|  | Initial | RT 3 months | 37/75 3 months | RT 12 months | 30/80 12 months | 15 months | RT 24 months |
|---|---|---|---|---|---|---|---|
|  |  |  | FDA METHOD 80% At 60 Minutes |  |  |  |  |
| Example 12 | 10-15 | 9-14 | 26->60* | 12-17 |  | 26->60** |  |
| Example 2 | 5-22 |  | 5-8* |  |  |  | 6-16 |
|  |  |  | USP METHOD |  |  |  |  |
| Example 12 | (8.2) | (8.5) | (14.5) | (7.3) |  | (23)** |  |
| Example 2 | (5) |  |  | (6) | (8)*** | (7)** |  |

Dissolution time range in minutes for all tablets and the average in parentheses.
The initial, 3 month, and 12 month tests were the pre-1988 test procedure and the others used the post-1988 test procedure.
*The tablets were stored at 37° C. and 75% relative humidity for 3 months.
**The tablets were stored at room temperature for 12 months and then stored at 37° C. and 75% relative humidity for three additional months.
***The tablets were stored at 30° C. and 80% relative humidity for 12 months.